United States Patent [19]

Pentoney, Jr. et al.

[11] Patent Number: 5,484,571
[45] Date of Patent: Jan. 16, 1996

[54] ENHANCED FLUORESCENCE DETECTION OF SAMPLES IN CAPILLARY COLUMN

[75] Inventors: Stephen L. Pentoney, Jr., Yorba Linda, Calif.; Wilbur Kaye, Princeville, Hi.

[73] Assignee: Beckman Instruments, Inc., Fullerton, Calif.

[21] Appl. No.: 264,417

[22] Filed: Jun. 23, 1994

Related U.S. Application Data

[63] Continuation of Ser. No. 772,823, Oct. 8, 1991, abandoned.

[51] Int. Cl.[6] .......................... G01N 21/31; G01N 21/01; G01N 27/447
[52] U.S. Cl. ..................................... 422/82.08; 422/82.05; 204/299 R; 204/180.1
[58] Field of Search .............................. 422/82.08, 82.07, 422/82.05, 82.11, 68.1, 82.09, 55, 91; 356/344, 318, 73, 51, 44, 343, 85; 250/264.65, 306, 361 C; 204/299 R, 180.1

[56] References Cited

U.S. PATENT DOCUMENTS

| | | | |
|---|---|---|---|
| 3,795,450 | 3/1974 | Munk | 356/246 |
| 3,985,441 | 10/1976 | Schoeffel et al. | 356/88 |
| 4,088,407 | 5/1978 | Schoeffel | 356/246 |
| 4,172,227 | 10/1979 | Tyrer et al. | 250/461 |
| 4,199,686 | 4/1980 | Brunsting et al. | 356/342 |
| 4,273,443 | 6/1981 | Hogg | 356/343 |
| 4,367,040 | 1/1983 | Goto | 356/44 |
| 4,565,448 | 1/1986 | Abbott et al. | 356/336 |
| 4,657,397 | 4/1987 | Oehler et al. | 356/414 |
| 4,675,300 | 6/1987 | Zare et al. | 436/172 |

(List continued on next page.)

FOREIGN PATENT DOCUMENTS

| | | | |
|---|---|---|---|
| 0404646 | 12/1990 | European Pat. Off. | G01N 27/447 |
| 2558262 | 7/1985 | France | G01B 33/483 |
| 56-37957 | 9/1982 | Japan. | |
| 63-303176 | 6/1990 | Japan. | |
| 63303174 | 6/1990 | Japan. | |
| 330564 | 9/1990 | Japan. | |
| 1128361 | 10/1965 | United Kingdom. | |
| 2155176 | 9/1985 | United Kingdom. | |

OTHER PUBLICATIONS

Pentoney, S. L. Jr., Huang, X., Burgi, D., & Zare, R. N.; "On–Line Connector For Microcolumns: Application to the On–Column o–Phthaldialdehyde Derivatization of Amino Acids Separated by Capillary Zone Electrophoresis"; Anal. Chem. 1988, 60, pp. 2625–2629.

Folestad, S., Johnson, L. & Josefsson, B.; "Laser Induced Fluorescence Detection for Conventional and Microcolumn Liquid Chromatography"; Anal. Chem. 1982, 54, pp. 925–929.

Folestad, S., Galle B., Josefsson, B.; "Small–Bore LC/Laser Fluorescence"; Journal of Chromatographic Science, vol. 23, Jun. 1985.

J. V. Sweedler, et al; "Fluorescence Detection in Capillary Zone Electrophoresis Using a Charge–Coupled Device with Time–Delayed Integration"; Analytical Chemistry, vol. 63, No. 5, Mar. 1991, pp. 496–502.

(List continued on next page.)

*Primary Examiner*—James C. Housel
*Assistant Examiner*—Michael L. McGlashen
*Attorney, Agent, or Firm*—William H. May; Paul R. Harder; Schneck & McHugh

[57] ABSTRACT

A simple device for collecting a greater amount of fluorescent emission from a minute sample in a capillary column. An axially symmetrical paraboloid reflector is implemented to collect fluorescent emission from the capillary column. The reflector also serves as a simple bracket for positioning and aligning the capillary column. Fluorescent emission is collimated by the paraboloid reflector which allows more effective use of band pass filters in blocking scattered radiation from detection. The scattered and transmitted radiation can be used to facilitate alignment of the capillary with respect to the detection optics. The paraboloid reflector also facilitates the implementation of simultaneous multiple-channel detection.

34 Claims, 6 Drawing Sheets

U.S. PATENT DOCUMENTS

| | | | |
|---|---|---|---|
| 4,786,171 | 11/1988 | LeFebre et al. | 356/326 |
| 4,801,552 | 1/1989 | Hoff | 422/82.09 |
| 4,838,688 | 6/1989 | Rhoads | 356/72 |
| 4,854,700 | 8/1989 | Cutie et al. | 356/72 |
| 4,927,265 | 5/1990 | Brownlee | 356/73 |
| 4,929,561 | 5/1990 | Hirschfeld | 422/82.07 |
| 4,997,275 | 3/1991 | Gaucher et al. | 356/72 |
| 5,062,942 | 11/1991 | Kambara et al. | 356/344 |
| 5,108,179 | 4/1992 | Myers | 356/318 |
| 5,292,483 | 3/1994 | Kaye et al. | 422/82 |

OTHER PUBLICATIONS

Bornhop, D. et al; "Simultaneous Laser–Based Refractive Index and Absorbance Determinations Within Micrometer Diameter Capillary Tubes"; *Anal. Chem.* (1987) pp. 1632–1637.

Herzenberg, et al; "Fluorescence–activated Cell Sorting"; Scientific American (1976), vol. 234, N3, pp. 108–117.

Pentoney, et al; "On–Column Radioisotope Detection"; developed from ACS Symposium Series No. 434, pp. 60–89.

ENHANCED FLUORESCENCE DETECTION OF SAMPLES IN CAPILLARY COLUMN

This is a continuation of application Ser. No. 07/772,823 filed on Oct. 8, 1991, now abandoned.

BACKGROUND OF THE INVENTION

1. Field of the Invention

The present invention relates to fluorescence detection and more particularly to the collection of fluorescent emission from a capillary separation channel.

2. Description of Related Art

Fluorescence detection is inherently very sensitive and macromolecules (e.g. proteins and DNA fragments) of a biological sample which have been labeled with fluorescent materials can be detected by analyzing the fluorescent emissions. Fluorescence detection has been practiced in the field of capillary electrophoresis. Reference is made to U.S. Pat. No. 4,675,300 to Zare et al for a detailed description of the detection technique. In general, Zare makes use of a coherent light source (e.g. laser) to interrogate a small portion of a capillary separation channel thereby defining a small detection volume. The samples being separated by electrophoresis have been tagged with fluorescent materials such as fluorescein prior to, during or just after electrophoresis. Upon electrophoresis, as the samples cross the path of the light beam, the fluorescent materials are caused to fluoresce thereby indicating the presence of a sample. By tagging the samples with appropriate fluorescent materials, one can detect the intensity of fluorescent emission from the separated samples and determine from the relative intensities the amount of a particular sample present in the sample mixture and its identity.

To date, laser-induced fluorescence is by far the most sensitive means of detecting many types of sample components separated by capillary electrophoresis. Because of the small detection volume, it is desirable to collect as much of the fluorescent emissions as possible to achieve maximum sensitivity. In the past, carefully corrected optics such as a large numerical aperture microscope objective or one or more optical fibers have been used to collect a relatively small solid angle of the fluorescent emission. In this case not only must the laser beam be in proper alignment with the capillary separation channel, but the capillary separation channel itself must be brought into proper alignment with the microscope objective. This necessitates the use of a translatable optical alignment component such as a capillary positioner or a microscope objective positioner. Since careful alignment of both the capillary separation channel with the laser beam and the collection optic (microscope objective or optical fibers) are essential in order to realize maximum sensitivity, typically at least two of the optical components have been mounted on translatable platforms in order that the system may be brought into optimum alignment.

The design of the collection optic system must also take into consideration the undesirable scattered radiation at the source frequency which is typically much more intense than the fluorescent emission. It is known that there is a bright plane of scattered radiation at the source frequency which is distributed over a 360° angle about and perpendicular to the capillary column. Because it is necessary to minimize the amount of scattered radiation reaching the photodetector, in the past some optical systems have been configured to collect emissions which are out of this plane of scatter.

SUMMARY OF THE INVENTION

The present invention is directed to a simple and inexpensive means of collecting a greater amount of fluorescent emission from a minute sample in a capillary column. An axially symmetrical paraboloid reflector is implemented to collect fluorescent emission from the capillary column. The reflector also serves as a simple bracket for positioning and aligning the capillary column. Fluorescent emission is collimated by the paraboloid reflector which allows more effective use of band pass filters in blocking scattered radiation from detection. Either the scattered radiation or the transmitted excitation beam, or both, can be used to facilitate alignment of the laser beam with respect to the capillary column and paraboloid focal point. The paraboloid reflector also facilitates the implementation of simultaneous multi-channel detection schemes.

BRIEF DESCRIPTION THE DRAWINGS

DESCRIPTION OF THE ILLUSTRATED EMBODIMENTS

The following description is of the best presently contemplated mode of carrying out the invention. This description is made for the purpose of illustrating the general principles of the invention and should not be taken in a limiting sense. The scope of the invention is best determined by reference to the appended claims.

While the present invention is described hereinbelow in reference to capillary electrophoresis, it is however understood that the present invention is not limited to such application but is applicable to fluorescence detection of samples in capillary column in general.

Figure 1:
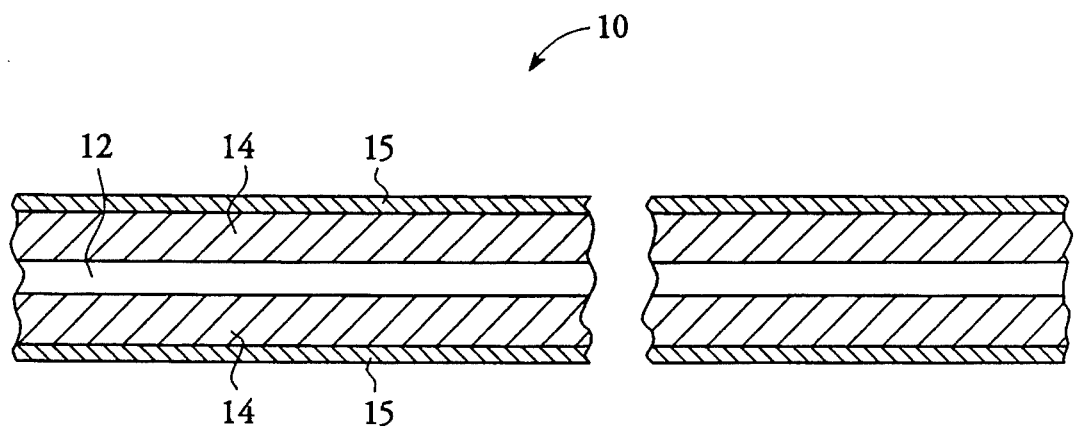
FIG. 1 is a diametral sectional view of a capillary tube.

A capillary tube 10 is shown in diametral sectional view in FIG. 1. The tube defines a cylindrical separation channel 12 of capillary dimension on the order of 5–500 micron, typically less than 200 micron. The cylindrical wall 14 of the capillary tube 10 can be made of glass, fused silica, or organic material such as teflon. To strengthen the wall 14, a polyamide coating 15 is bonded to its external surface. The capillary tube 10 is generally flexible, i.e. can be bent into smooth curves.

Figure 2:
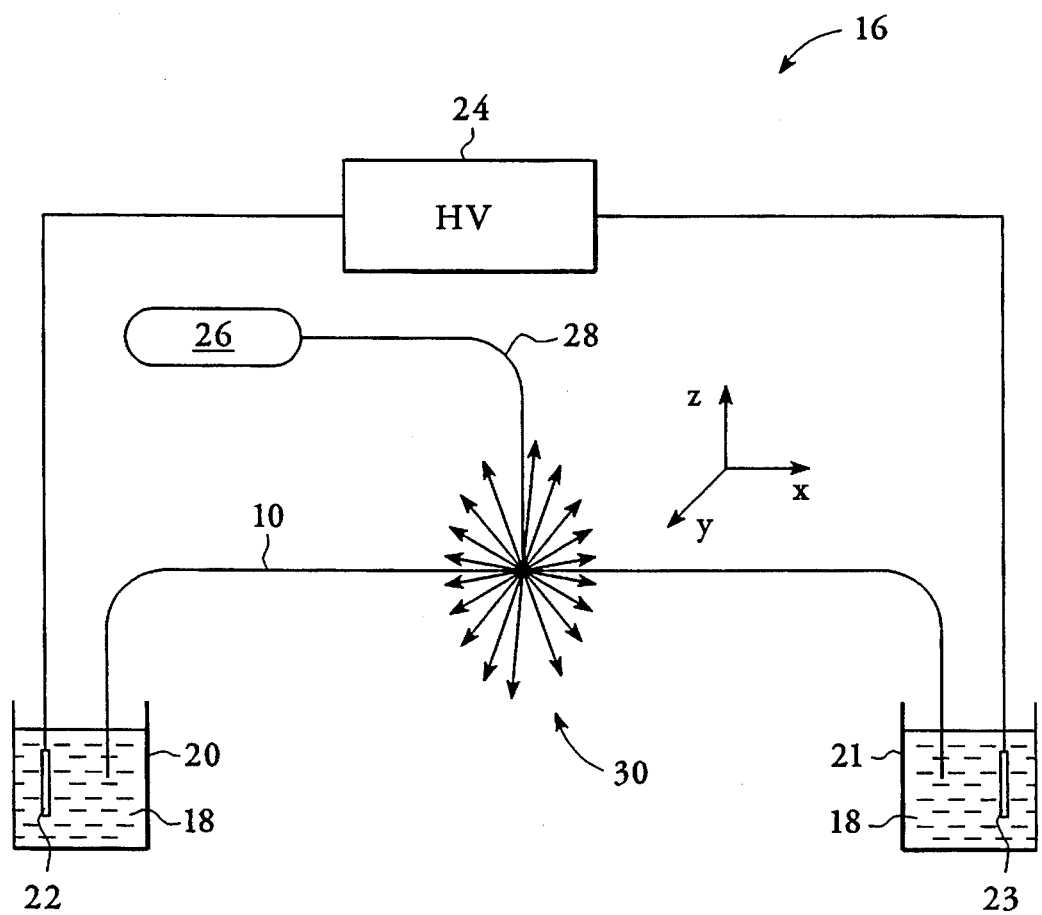
FIG. 2 is a schematic of a capillary electrophoresis apparatus with laser induced fluorescence detection.

FIG. 2 illustrates a schematic arrangement of a capillary electrophoresis apparatus 16, and more particularly one in which detection is accomplished by laser induced fluorescence. The two ends of the capillary tube 10 are submerged in electrolyte 18 contained in reservoirs 20 and 21. A high voltage power supply 24 capable of applying a high electric field (typically 1–30 KV) is electrically connected to the electrolyte 18 in the reservoirs 20 and 21 using electrodes 22 and 23. The separation channel is filled with a separation support medium which may be a electrolyte solution, gel electrolyte or other suitable conductive medium. Prior to electrophoresis, a sample to be electrophoretically separated is injected into one end of the separation channel 12. This can be done by any number of conventional techniques. With the two ends of the capillary tube 10 dipped into the electrolyte 18, the high voltage power supply 24 is turned on to cause electrophoresis of the sample which results in separation into its components.

In order to be able to detect fluorescence of the separated components of the sample, it is tagged with a fluorescent material such as fluorescein. For laser induced fluorescence detection, a laser 26 is used as the excitation source. The laser 26 can be, for example, an air cooled argon ion laser, a helium-cadmium laser or a HeNe laser having an output in the range of 1–100 milliwatts. A focusing lens (not shown in FIG. 2) or an optical fiber 28 may be used to direct the laser output to a detection section along the capillary tube 10. At this section, the polyimide protective coating 15 has been removed to allow the laser light to pass through the capillary wall 14 to the separation channel 12. Instead of using a laser source, other radiation sources can be used to excite fluorescence of the fluorescent tags in the sample components.

The laser beam is directed at 90° to the capillary tube 10. When the sample components pass by the laser beam, they are caused to fluoresce in all directions 30. It is desirable to collect and detect as much of the fluorescence as possible to maximize sensitivity and signal-to noise.

Figure 3:
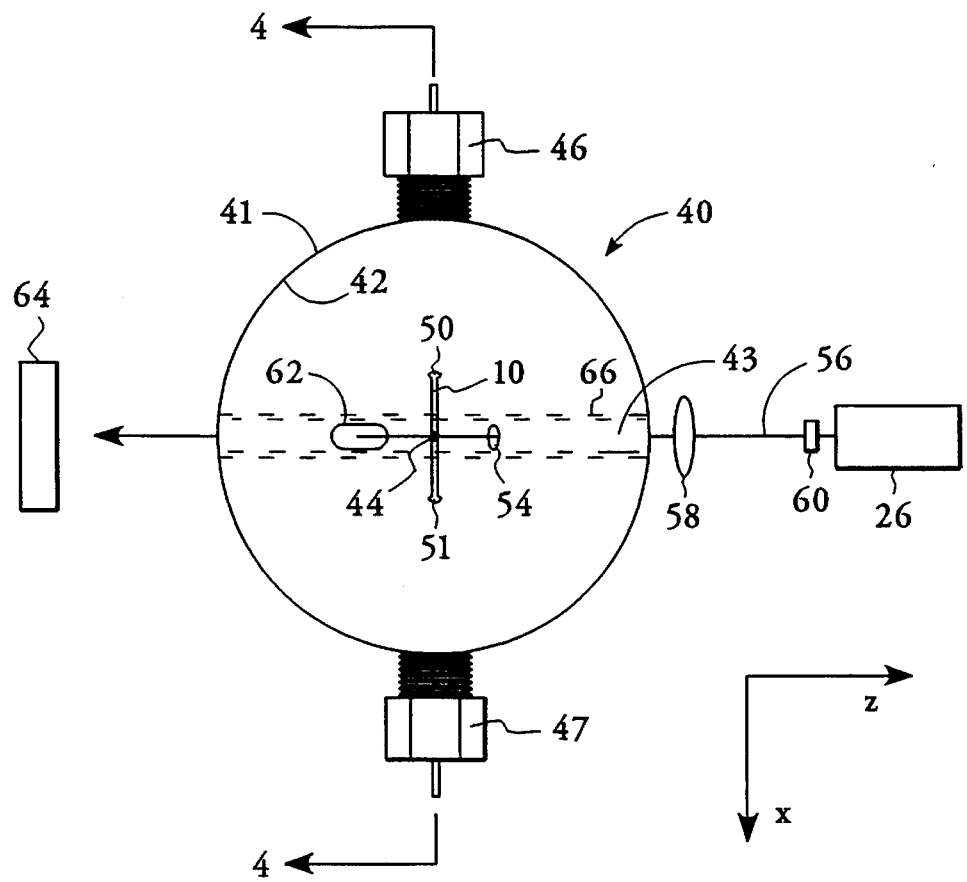
FIG. 3 is a schematic of a paraboloid reflector used in laser induced fluorescence detection in accordance with one embodiment of the present invention.
Figure 4:
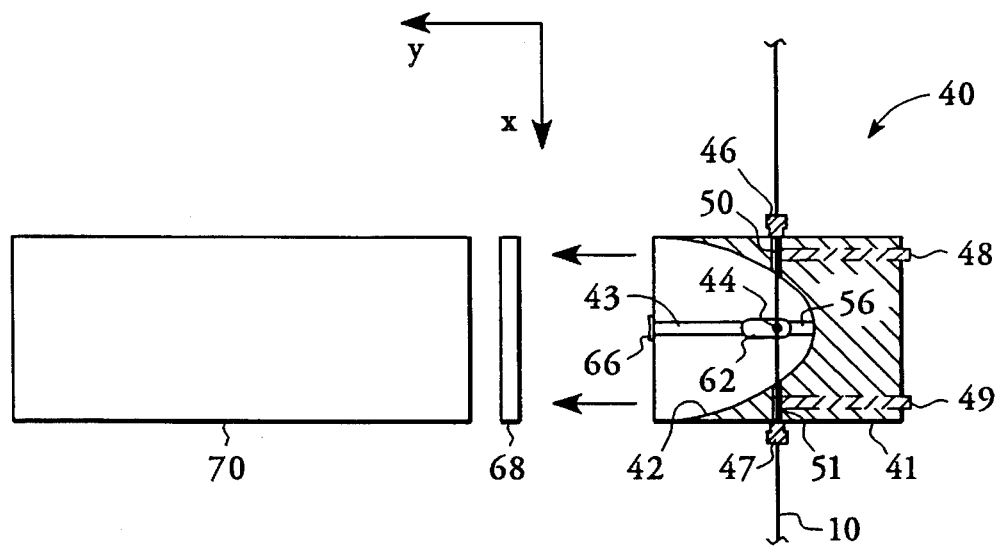
FIG. 4 is a sectional view along line 4—4 in FIG. 3 and includes a photodetector and emission filter.

The present invention implements a concave reflector which focuses on the detection section of the capillary tube 10. In the illustrated embodiment, the reflector is an axially symmetrical concave paraboloid reflector. Referring to FIGS. 3 and 4, the configuration of the fluorescence collection and detection optics are schematically illustrated. The paraboloid reflector 40 is shown as formed from a cylindrical body 41. This can simply be a polished paraboloid surface 42 of an aluminum block or a metalized paraboloid mirror surface of a plastic block. The block structure allows easy attachment of fittings for securely mounting the capillary tube 10.

The capillary tube 10 is threaded through through-holes 50 and 51 provided in the sides of the reflector body 41. The holes 50 and 51 are positioned such that the capillary tube passes through the focal point 44 of the paraboloid reflector; in particular the detection section of the capillary separation channel is positioned at the focal point 44 of the paraboloid reflector 40. Fittings 46 and 47 are provided to securely mount the capillary in this position. In the alternate or in addition, set screws 48 and 49 may be used through the rear of the reflector to lock the capillary tube 10 in place.

The reflector body 41 is also provided with through-hole 54 through which a laser beam 56 can pass at right angles to the capillary tube 10. The laser beam 56 may be directed at the detection section of the capillary tube 10 by use of a optical fiber 28 (FIG. 2) through the hole 54, or a lens 58 focusing the laser beam 56 through the hole 54 (FIG. 3). Alternatively, the laser beam may be directed from the front of the paraboloid if there is an opening through the vertex of the reflector to allow the transmitted beam to pass (see FIG. 6).

In the embodiment shown in FIG. 3, an excitation filter 60 is used to attenuate any light of unwanted wavelengths originating from the laser 26. In line with the laser entrance hole 54, there is an exit hole 62 provided on the body 41 of the reflector 40. This hole 62 is sized large enough to allow passage of the most intense portion of the transmitted and scattered laser light in the plane perpendicular to the capillary. The exit hole 62 is in the shape of a slot having its larger width in the axial direction of the reflector 40 since the scattered light is in a plane perpendicular to the capillary tube 10. A laser beam dump 64 is provided to trap the light transmitted through the exit hole 62 to prevent the light from interfering with the adjacent detection optics. The beam dump 64 may be nothing more than a piece of paper upon which the transmitted light may be viewed for purpose of lateral alignment of the capillary tube 10 and the incident laser beam. When properly aligned, a symmetric pattern of scattered light is observed upon the beam dump. The use of scattered light for capillary tube alignment is described in detail in U.S. Pat. No. 5,208,466 commonly assigned to the assignee of the present invention and is incorporated herein by reference.

In order to mask the scattered light which is reflected from the reflector 40 and/or scattered directly from the capillary tube 10 toward the photomultiplier tube 70, a thin strip 66 of opaque material is mounted over the mouth of the paraboloid reflector 40 and obstructs the plane of scatter. This plane of scatter is normal to the capillary axis. To further reduce the amount of scattered light directed to the photomultiplier tube, the reflector 40 and strip 66 are lined, i.e. glued, with a light absorbing material 43, e.g. flocking paper, about the scatter plane as shown in FIG. 4.

Fluorescent light from the detection section is collimated by the paraboloid reflector 40 and then passes through an emission filter 68 for passing fluorescence of a particular wavelength (further blocking any remaining scattered light) and onto a photomultiplier tube 70. The diameter of the end window of the photomultiplier tube 70 should be approximately equal to the mouth diameter of the reflector 40. The emission filter 68 and excitation filter 60 must not allow a common wavelength to pass to the photomultiplier tube 70 in order to be able to block scattered light at source wavelength.

In order for proper collimation of the fluorescence emission from the capillary detection section, the laser beam should be directed at the focus of the paraboloid. The X-direction alignment of the laser beam with the focus of the paraboloid is determined by looking at the position of the shadow of the blocking strip 66 in the collimated beam. This is described in the U.S. Pat. No. 5,208,466 which has been incorporated by reference herein. Generally, the laser beam is properly aligned with the focus of the paraboloid when the shadow of the blocking strip 66 is centrally located in the collimated image.

It is noted that the paraboloid reflector serves a dual purpose. It is both a highly efficient light collector/collimator and a capillary support. The paraboloid reflector 40 provides a much simpler and less expensive means of collecting a greater amount of the fluorescent emission from the sample irradiated by the laser beam 56. The reflector 40 allows collection of a greater solid angle of rays emanating from the sample than with an objective lens system. For example, large numerical aperture microscope objectives used in the past currently cost on the order of one hundred dollars, and collect about 10% of the fluorescent emission. While the paraboloid reflectors described herein are available on the order of five dollars from Carley Lamps, and collect on the order of 40–50% of the fluorescent emission. The collimated fluorescent light allows more effective use of bandpass filters in removing scattered radiation, because bandpass filters require irradiation normal to their surface for proper spectral filtering.

The paraboloid body 41 effectively secures the position of the capillary tube 10 at the focal point. As a result, the number of optical components required for laser induced fluorescence detection in a capillary electrophoresis system have been reduced. Alignment of the capillary with respect to the fluorescence collector is simplified, as a microscope objective is not required.

It is noted that excitation sources other than a laser could be substituted. Detectors other than the photomultiplier may be utilized. In particular a silicon detector could be used in which case there might be merit in substituting an ellipsoid for a paraboloid so that the fluorescence can be collected and focused onto the silicon detector.

Figure 5:
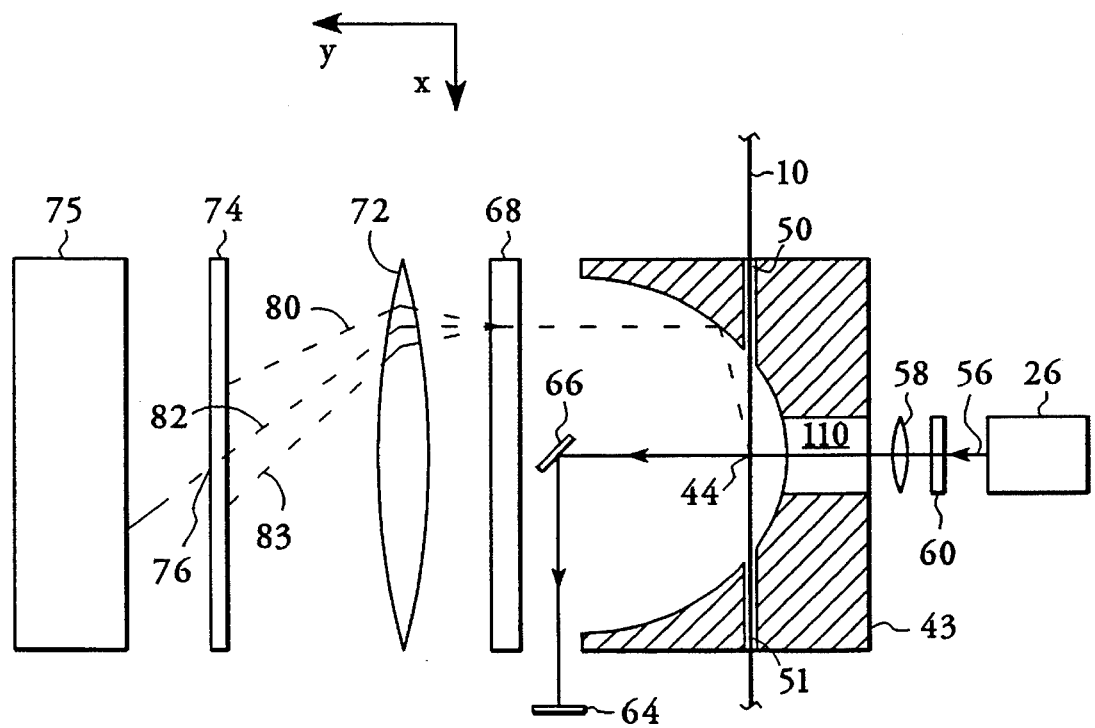
FIG. 5 is a schematic illustrating focusing of the collimated beam to an aperture plate.

The aforedescribed configuration can be improved by the addition of a lens and aperture facing the reflector. The basic concept is schematically shown in FIG. 5 (some items have been omitted for simplicity). Laser beam 56 from laser 26 is filtered by excitation filter 60 and focused by lens 58 onto the sample in capillary 10 at the focus 44 of the paraboloid 43. A hole 110 in the rear and axial to the paraboloid 43 allows the beam to pass into the paraboloid. Holes 50 and 51 drilled into the paraboloid hold the capillary at the focus of the paraboloid. Upon striking the capillary, a significant fraction of the beam is scattered in a plane perpendicular to the capillary. The primary beam and part of the forward scattered beam is reflected by a mirror 66 positioned along the axis of the paraboloid onto a translucent screen 64. As the beam is focused by lens 58, a symmetric pattern of scatter will be seen on the screen 64 (see U.S. Pat. No. 5,208,466 which has been incorporated herein by reference). The remainder of the scattered rays will be trapped by a black bar across the mouth of the paraboloid. This bar (not shown in FIG. 5) also supports the mirror 66 at the axis of the paraboloid.

The fluorescent rays originating from a sample at focus 44 are collimated by the paraboloid and pass to the emission filter 68. One of these rays is identified as 80. Those rays 82 that pass through filter 68 perpendicular to the filter face will be imaged by lens 72 and pass through an aperture 76 on plate 74 to a detector 75. The cone of rays 83 having a wavelength of the exciting laser will fall on the aperture plate 74 and not pass to the detector 75.

If an ellipsoidal reflector is used (not shown), the aperture 76 is located at the second focus of the ellipsoidal reflector. However, there is no region where a collimated beam exists in an ellipsoidal system. Therefore there is greater flexibility in the location of optical components in the paraboloidal system. The lens may abut the paraboloid or be placed at a distance.

There are several advantages resulting from the addition of the lens 72 and aperture 76. The lens and aperture constitute a spatial filter. Stray light originating anywhere other than the focus of the paraboloid reflector 40 will be blocked by the plate 74. In particular, rays that scatter off the paraboloid reflector 40 at any angle other than its specular angle will be blocked. Also the fluorescence source, i.e. the sample, will be imaged on the plate 74. If the source is of extended size the aperture 72 will define the portion of the source from which fluorescence rays may be detected.

Another advantage of the improvement is that the focused beam 82 will have a higher flux density than the collimated beam 80. This means that solid state detectors such as light sensitive diodes will respond with better signal-to-noise than the unfocused case. If one uses magnetic focusing of a photomultiplier, even it will exhibit superior signal-to-noise.

Figure 6:
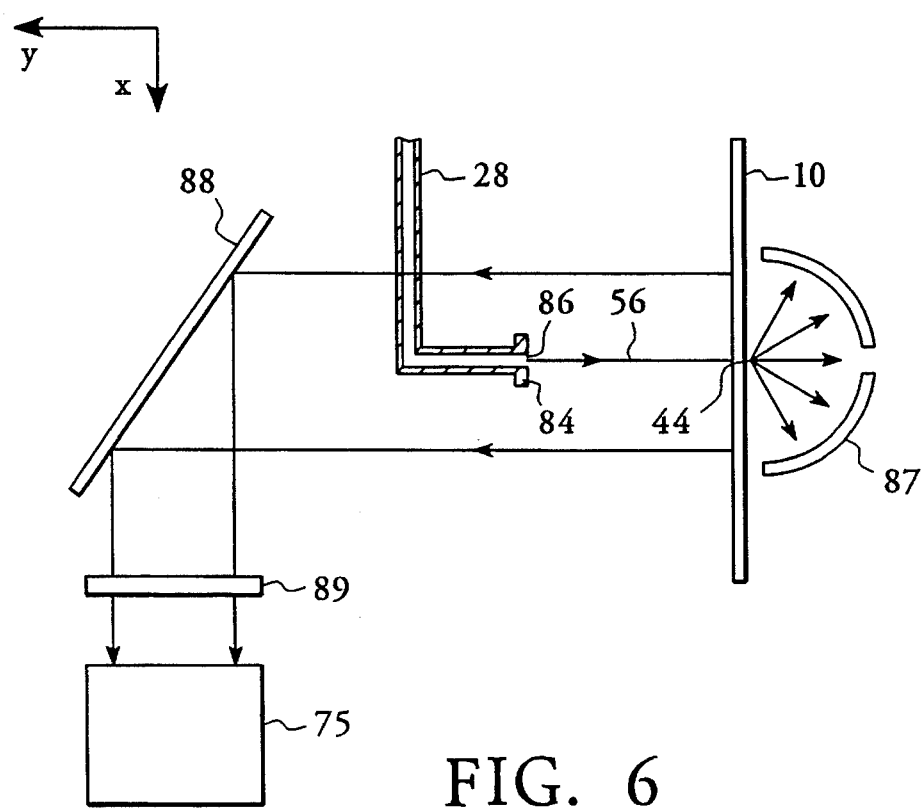
FIG. 6 is a schematic illustrating another embodiment of the laser and reflector configuration.

FIG. 6 illustrates an alternate configuration of irradiation of the capillary 10. In this configuration, the laser beam 56 is directed head-on towards the paraboloid reflector 87 along its axis. The tip of optical fiber 28 is positioned against an aperture 86 on a blocking strip 84 and the laser beam is directed at the focus 44 of the paraboloid 41 where the detection section of the capillary 10 is positioned. The emitted fluorescence is collimated and reflected by a mirror 88, passed through a filter 89, and directed at the photomultiplier 75. A focusing lens and aperture may be added to this configuration (not shown) to accomplish the advantages of the embodiment of FIG. 5.

The paraboloid reflector further facilitates implementation of several detection channels for simultaneous detection. Some types of samples are best detected by analyzing the absorbance of ultraviolet ("UV") radiation while others are sensitively detected by fluorescence. Moreover, some samples may be tagged with different types of dyes that fluoresce and/or absorb at different wavelengths. For example there is a particular need for multiple wavelength detection when studying DNA.

Figure 7:
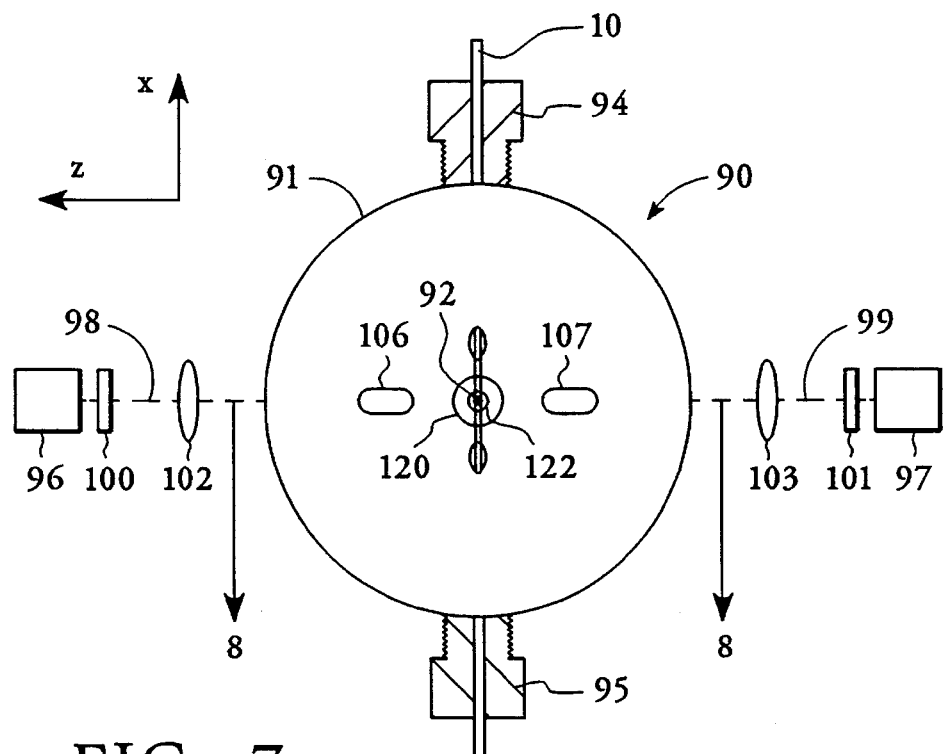
FIG. 7 is a schematic illustrating a multiple-channel detection configuration in accordance with one embodiment of the present invention.
Figure 8:
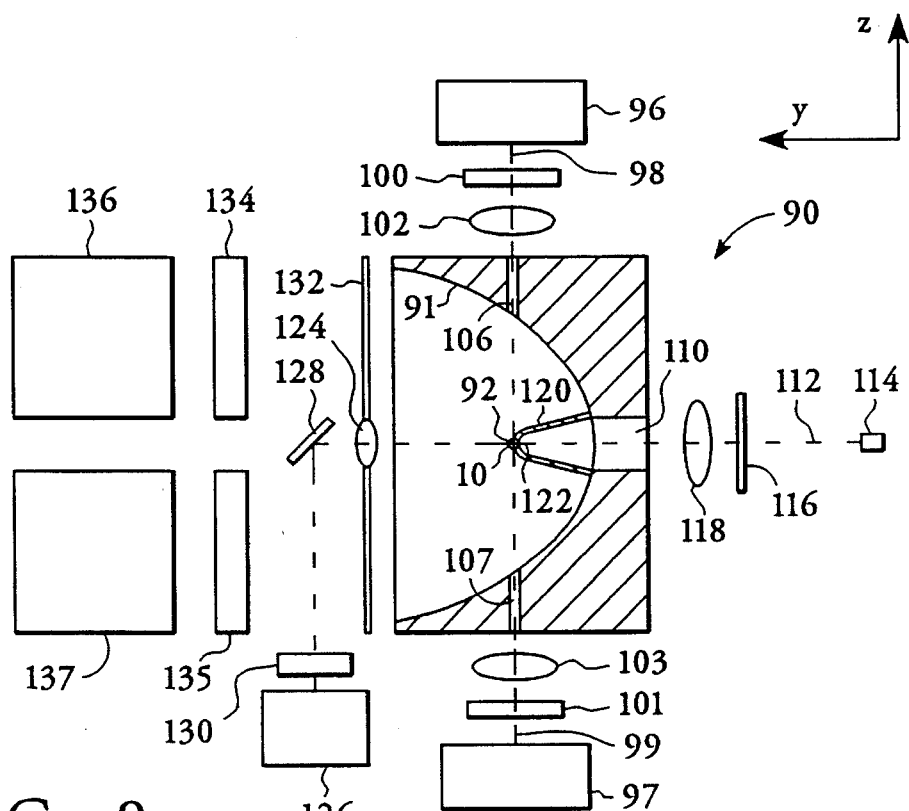
FIG. 8 is a sectional view along line 8—8 in FIG. 7.

The following is a description of a multiple-channel detection system, in particular one incorporating laser induced fluorescence and UV absorption. FIGS. 7 and 8 schematically illustrate the multiple detection configuration in accordance with one embodiment of the present invention. As in the embodiment described with reference to FIGS. 3 and 4, the capillary tube 10 is threaded through the body 91 of the paraboloid reflector 90 and passes through the focal point 92 of the paraboloid reflector 90. Specifically, the intended detection section along the capillary tube 10 is positioned at the focal point 92 of the paraboloid reflector 90. Two mounting nuts 94 and 95 hold the capillary tube 10 in place. In this embodiment, there are two laser sources 96 and 97 having their beams 98 and 99 filtered by filters 100 and 101 and focused by lenses 102 and 103 onto the capillary tube 10 at the focal point 92 of the paraboloid reflector 90. Holes 106 and 107 are provided in the body 91 of the reflector 90 for passage of the laser beams 98 and 99. When the laser beams 98 and 99 are of the same wavelengths, the angle between the two laser beams 98 and 99 in a horizontal plane is not exactly 180° to avoid optical feedback. When the laser beams 98 and 99 are of different wavelengths, the beams may be exactly 180° apart in a horizontal plane (as in FIG. 7 and 8) without concern for feedback since the two exciting filters 100 and 101 would then not pass the same wavelengths.

Provision is made for UV absorption detection. Referring to FIG. 8, an axial hole 110 is provided in the base of the reflector body 91 to allow passage of UV beam 112 from a UV source 114, (e.g. deuterium lamp) to the focal point 92. The UV beam 112 is filtered by a filter 116 and focused by a lens 118 onto the detection section of the capillary tube. A conical shaped mask 120 projects out from the axial hole 110 and terminates at the capillary tube 10. A hole 122 having a diameter smaller than that of the capillary separation channel is drilled in this conical mask 120 at its apex and serves to define the portion of the UV beam 112 passing through to the capillary separation channel. Lens 124 focuses the beam transmitted through the capillary onto the detector 126 via mirror 128 and filter 130. This lens 124 is supported on a strip 132 of metal running across the mouth of the paraboloid reflector 90 perpendicular to the capillary tube 10. The strip blocks the intense laser rays scattered from the capillary tube 10. Filter 130 passes the same UV wavelengths as filter 116 and thereby eliminates rays scattered and fluoresced by the sample from being detected by the detector 126. It should be noted that the UV beam 112 is essentially noncoherent, hence must be defined by a much larger solid angle than the two laser beams 98 and 99.

The fluorescence of the sample is collected and collimated by the paraboloid reflector 90. In the configuration shown in FIG. 8, the light from the upper half of the reflector 90 passes through filter 134 and onto detector 136 while the light from the lower half of the reflector 90 passes through filter 135 and onto detector 137.

In the configuration of FIG. 8, it is intended that the three channels (laser beams 98 and 99 and UV beam 112) be detected simultaneously. Performance in this configuration will be limited by cross-talk in the three channels. It must be recognized that the fluorescence emission intensity in the fluorescence channels are much less than the UV intensity in the absorbance channel. Also, no UV radiation can pass through filters 134 and 135, but the UV radiation passing through filter 116 may excite fluorescence at wavelengths passed by filters 134 and 135. Fortunately, the intensity of the UV beam 112 is nowhere near as intense as the laser beams 98 and 99 and the quantum efficiency of fluorescence from the UV radiation can be expected to be much lower than that at the laser frequencies. Consequently, the fluorescence originating from UV excitation will be small relative to that originating from laser excitation. However, filter 130 may be of the absorption type and may exhibit a significant transmittance at the wavelengths of the intense laser sources.

Figure 9:
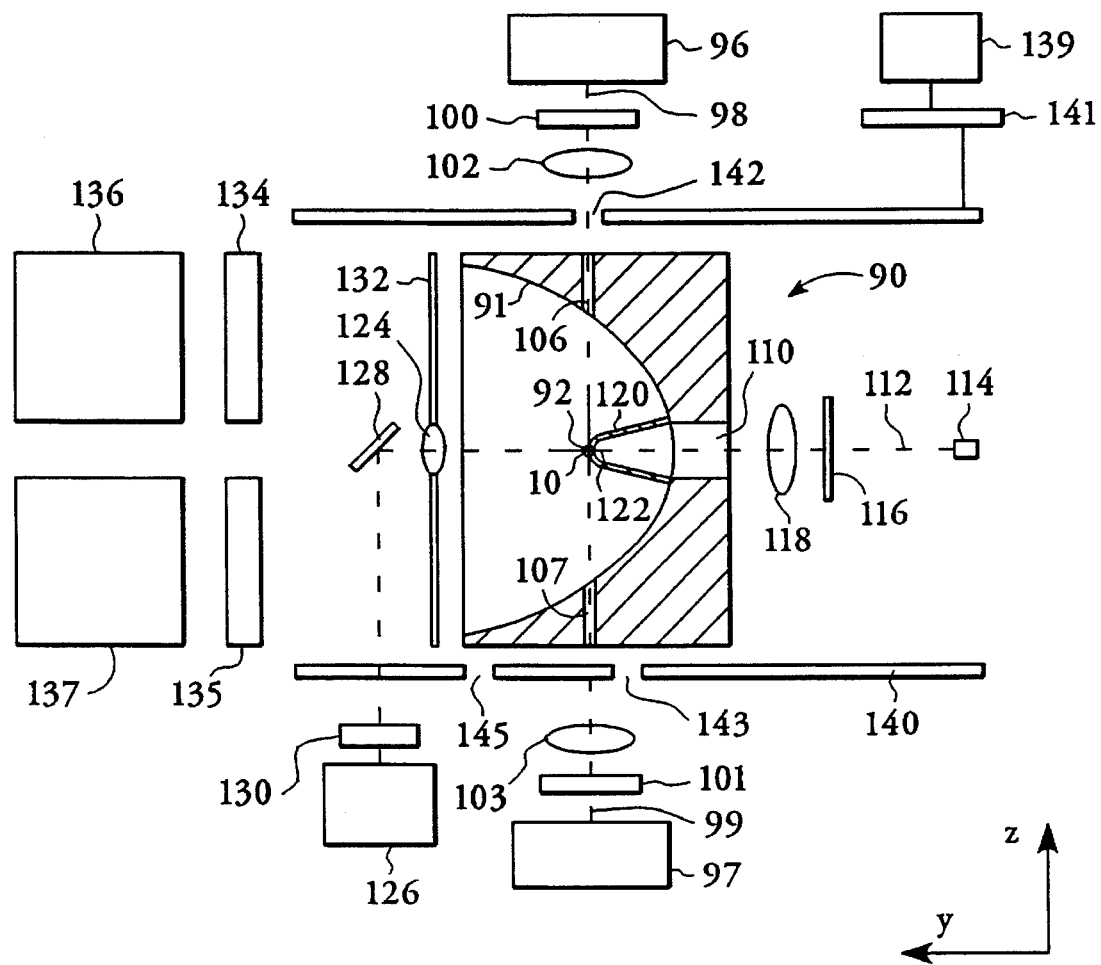
FIG. 9 shows the use of a cylindrical mask to switch passage of and ultraviolet beams to avoid cross talk.

The problem of cross-talk can be overcome by temporal masking of the radiation sources and/or the detector 126. FIG. 9 shows such a configuration, wherein a cylinder 140 is translated along the axis of the paraboloid reflector 90 by means of a motor 139 and a conventional eccentric drive mechanism 141. Apertures 142 and 143 in this cylinder 140 permit passage of beams 98 and 99 from the two laser sources 96 and 97 to the sample at different times while allowing simultaneous UV detection. However, shown in FIG. 9, to prevent crosstalk between the laser sources 96 and 97 and the UV source 114, the cylindrical mask 140 extends to block the UV detector 126. During a portion of each translation of the cylindrical mask 140, both laser beams 98 and 99 are blocked while allowing the detector 126 to sense the UV beam 112 through aperture 145. During another period, the detector 126 is blocked by cylindrical mask 140 when the sample is alternately irradiated by the lasers. The sample, however, is still exposed to the UV beam 112 during the period of laser exposure. In a further modification, the positions of the detector 126 and the UV source 114 are reversed (not shown). In this way, the simple translating cylinder allows the sample to be exposed to the three sources at three different intervals of translation of the cylinder. The latter two configurations, however, do not allow simultaneous detection using both laser and UV sources.

More than three channels of detection can be envisioned. For example, either or both of the lasers may emit more than one frequency of intense coherent light. Furthermore, it may be noted that more than two lasers can simultaneously illuminate the capillary tube so long as these lasers are positioned in a plane normal to the axis of the capillary tube.

Figure 10:
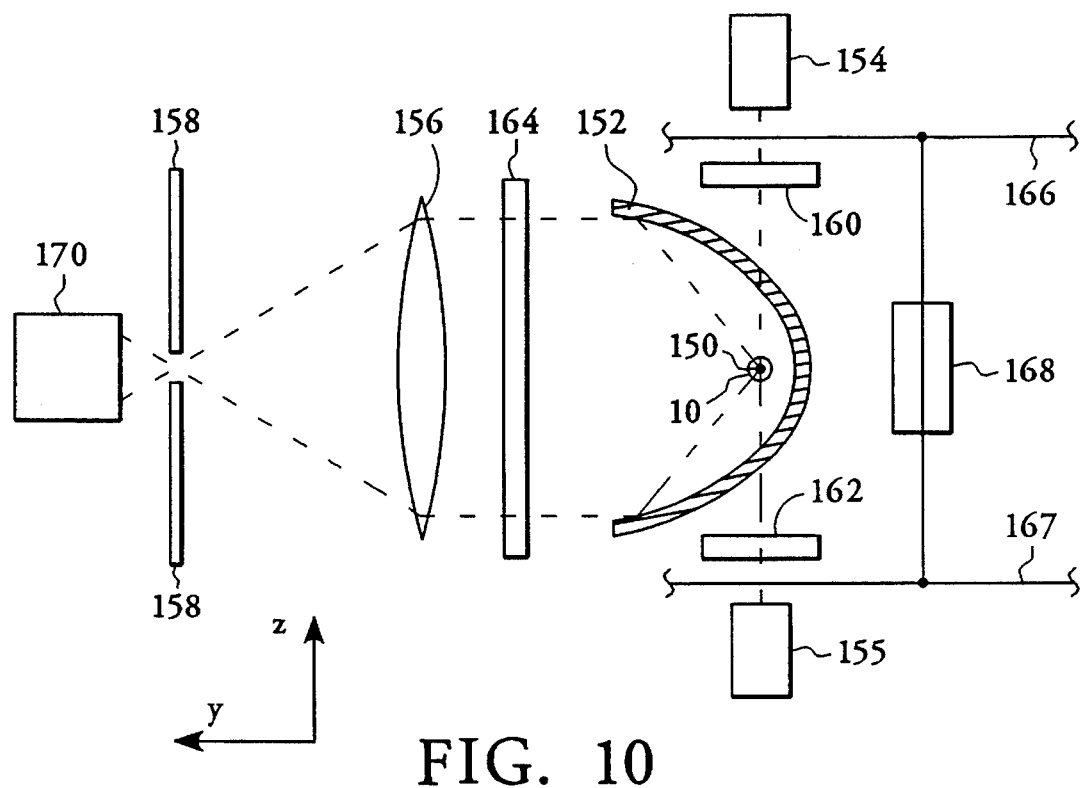
FIG. 10 is a schematic illustrating the configuration in which the sample is alternately exposed to laser beams of different wavelengths.

FIG. 10 shows another embodiment of multiple wavelength laser excitation. Fluorescence radiation originating from the sample in the capillary tube 10 at the focal point 150 as excited by laser sources 154 and 155 is focused by the paraboloid reflector 152, filtered by filter 164 and focused by lens 156 onto an aperture plate 158. Filters 160 and 162 allow only radiation of the desired wavelength to fall on the sample at the focal point 150. Partially rotating shutters 166 and 167 driven by a motor 168 alternately exposes the sample to radiation from the two sources 154 and 155. Filter 164 removes the exciting radiation so that a detector 170 located to the left of the aperture plate 158 responds only to fluorescence radiation. It should be obvious that filter 164 may also be a composite filter (e.g. a wheel having filters of various wavelength positioned about its axis) rotating synchronously with shutters 160 and 162. In this way the detected signal may be sorted for both excitation and fluorescent emission wavelengths. The advantages of using the aperture plate 158 has been previously discussed with reference to FIG. 5.

Figure 11:
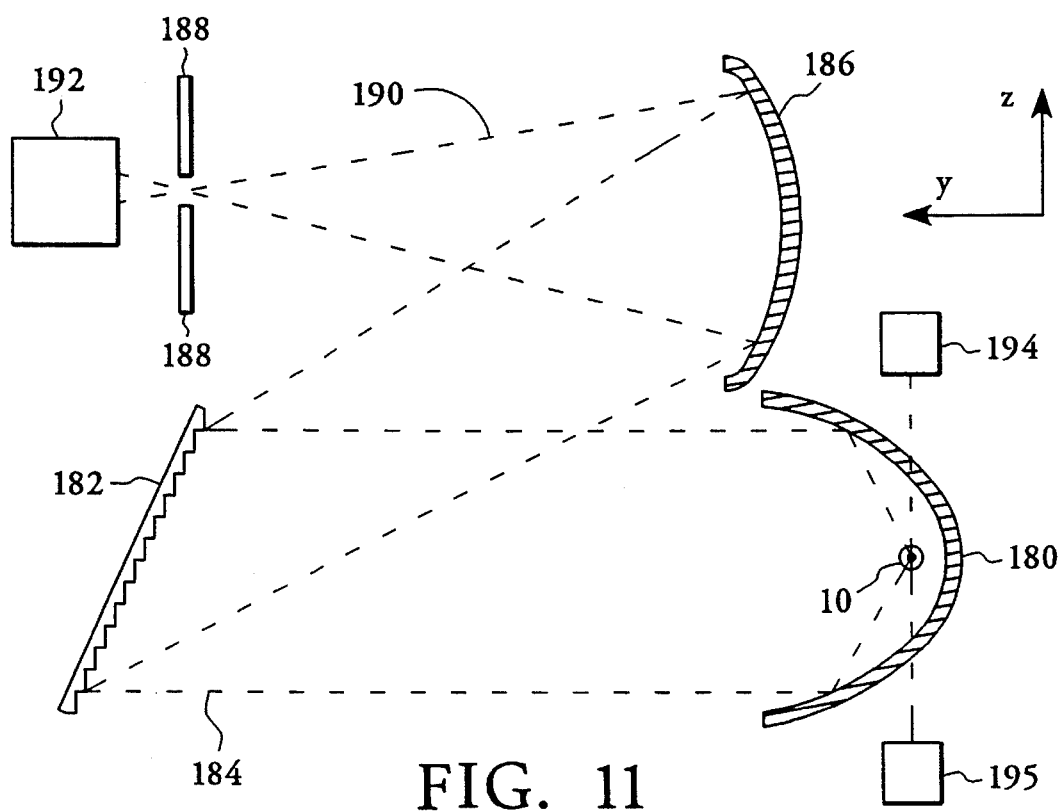
FIG. 11 is a schematic illustrating the use of diffraction grating in the collimated beam.

A further improvement of the above mentioned embodiments is shown in FIG. 11. A grating monochromator is positioned in the collimated beam 184 from the paraboloid reflector 180. A plane diffraction grating 182 intercepts the collimated beam 184 and radiation of a particular wavelength will diffract to mirror 186 from which it will be focused to an aperture on plate 188. After which the focused beam 190 may be detected using detector 192. Either by rotation of the grating 182 or translation of the aperture plate 188, a spectrum of radiation may be detected. As a refinement, a filter (not shown) may be placed in the collimated beam 184 to remove the intense laser excitation wavelengths. An array detector, i.e. diode array or charged-coupled device, may be substituted for the plate 188 and detector 192, thereby permitting the measurement of fluorescence spectrum without moving parts. The two excitation sources 194 and 195 may be shuttered by the mechanism shown in FIG. 10.

As a further modification of the system in FIG. 11, the aperture plate 188 may be tailored to allow a specific wavelength interval of fluorescence radiation to be detected. The system need not be limited to one wavelength interval. Two or more intervals may be sensed either with one or more detectors. The signals may be either spatially or temporally sorted. In some cases it may be possible to tailor one aperture (and detector) to respond to Raman signal (characteristic signal in capillary electrophoresis) and with proper attenuation allow compensation for this complicating factor.

While the invention has been described with respect to the illustrated embodiments in accordance therewith, it will be apparent to those skilled in the art that various modifications and improvements may be made without departing from the scope and spirit of the invention. Accordingly, it is to be understood that the invention is not to be limited by the specific illustrated embodiments, but only by the scope of the appended claims.

We claim:
1. An apparatus for collecting and detecting fluorescent emission of a sample migrating within a capillary separation channel defined by a capillary tube comprising:

an axially-symmetrical concave fluorescence collector having a convex reflective surface, and defining a focal point and a mouth, the body of the collector having holes through which the capillary tube passes, the capillary tube being positioned such that the sample migrates within the capillary tube past the focal point, the capillary tube being oriented at approximately a right angle to the axis of the collector;

irradiation means for irradiating the sample as it migrates within the capillary tube past the focal point so as to cause the sample to emit fluorescence, some of the fluorescence being reflected off the reflective surface of the collector and substantially all of the fluorescence emanating from the mouth of the collector, the body of the collector having at least one hole through which the radiation from the irradiation means passes, the irradiation means being positioned with respect to the capillary tube and the collector much that radiation from the irradiation means irradiates the sample within the capillary tube at the focal point at a right angle to the capillary tube directly without first reflecting from the reflective surface of the collector, wherein irradiation of the sample directly by the irradiation means causes radiation from the irradiation means to scatter from the capillary tube in a scatter plane normal thereto, some of the scattered radiation being directed along with the emitted fluorescence onto the reflective surface, detection means for detecting radiation emitted from the sample including the reflected fluorescence; and spatial blocking means for blocking scattered radiation from reaching the detection means, the spatial blocking means comprising an opaque blocking strip at the mouth of the collector, the spatial blocking means intersecting the axis of the collector and the scatter plane at the mouth of the collector but blocking only a minimal portion of the fluorescence at the mouth of the collector.

2. An apparatus as in claim 1 wherein the concave reflective surface of the collector has a parabolic shape to reflect fluorescence emitted from the sample at the focal point into a collimated beam.

3. An apparatus as in claim 1 wherein the irradiation means comprises a laser.

4. An apparatus as in claim 1 further comprising a filter which blocks radiation of undesired wavelength in the collimated fluorescence.

5. An apparatus as in claim 1 further comprising a plate having an aperture defined thereon for restricting the radiation detectable by the detection means, thereby blocking stray radiation.

6. An apparatus as in claim 1 further comprising means for separating collimated fluorescent radiation into a number of different wavelengths and directing a particular wavelength of radiation toward the detection means.

7. An apparatus as in claim 1 wherein the irradiation means includes a laser for generating first and second laser beams which are directed at the sample at the focal point of the collector.

8. An apparatus as in claim 7 further comprising means for alternately directing the first and second laser beams at the sample.

9. An apparatus as in claim 8 wherein the first and second laser beams are of different wavelengths.

10. An apparatus as in claim 8 wherein the first and second laser beams are at the same wavelength.

11. An apparatus as in claim 1 wherein the radiation from the irradiation means is directed through said at least one hole in the body of the collector toward the sample within the capillary tube at the focal point at a right angle to the axis of the collector, some radiation from the irradiation means being transmitted through the capillary tube and directed through another hole in the body of the collector.

12. An apparatus as in claim 1 wherein the radiation from the irradiation means is directed through said at least one hole in the body of the collector toward the sample within the capillary tube at the focal point along the axis of the collector, the irradiation means being positioned behind the collector with said at least one hole in the body located between the irradiation means and the focal point.

13. An apparatus as in claim 1 wherein the concave reflective surface of the fluorescence collector is shaped and configured to reflect fluorescence emitted from the sample at the focal point into a beam that converges at a convergence point beyond the mouth of the collector.

14. An apparatus as in claim 13 wherein the convergence point is on the detection means.

15. A capillary electrophoresis apparatus comprising:

a capillary tube defining a capillary separation channel through which sample components migrate;

means for causing electrophoresis of the sample into its components;

an axially symmetrical concave fluorescence collector having a concave reflective surface, and defining a focal point and a mouth, the capillary tube being positioned such that the sample components migrate past the focal point and oriented at approximately a right angle to the axis of the collector;

irradiation means for directly irradiating the sample components as they migrate within the capillary tube past the focal point so as to cause the sample components to emit fluorescence, some of the fluorescence being reflected off the reflective surface of the collector and substantially all of the fluorescence emanating from the mouth of the collector, the irradiation means being positioned with respect to the capillary tube and the collector such that radiation from the irradiation means irradiates the sample at a right angle to the capillary tube without first reflecting from the reflective surface of the collector, some of the radiation from the irradiation means being scattered from the capillary tube in a scatter plane normal thereto, some of the scattered radiation being directed along with the emitted fluorescence onto the reflective surface;

detection means for detecting radiation emitted from the sample components including the reflected fluorescence; and spatial blocking means for blocking scattered radiation from reaching the detection means, the spatial blocking mean comprising an opaque blocking strip at the mouth of the collector, the spatial blocking means intersecting the axis of the collector and the scatter plane at the mouth of he collector but blocking only a minimal portion of the fluorescence at the mouth of the collector.

16. An apparatus as in claim 15 wherein the concave reflective surface of the collector has a parabolic shape to reflect fluorescence emitted from the sample components at the focal point into a collimated beam.

17. An apparatus as in claim 15 wherein the radiation from the irradiation means is directed toward the sample components within the capillary tube at the focal point at a right angle to the axis of the collector.

18. An apparatus as in claim 15 wherein the radiation from the irradiation means is directed toward the sample components within the capillary tube at the focal point along the axis of the collector through a hole in the collector, the irradiation means being positioned behind the collector with the hole in the collector located between the irradiation means and the focal point.

19. An apparatus for multi-channel detection of a sample migrating in a capillary separation channel defined by a capillary tube comprising:

an axially-symmetrical concave fluorescence collector having a concave reflective surface, and defining a focal point and a mouth, the capillary tube being positioned such that the sample migrates past the focal point and being oriented at approximately a right angle to the axis of the collector;

first irradiation means for directly irradiating the sample within the capillary tube as the sample migrates past the focal point so as to cause the sample to emit fluorescence, some of the fluorescence being reflected off the reflective surface of the collector and substantially all of the fluorescence emanating from the mouth of the collector, the first irradiation means being positioned with respect to the capillary tube and the collector such that radiation from the first irradiation means irradiates the sample at a right angle to the capillary tube without first reflecting from the reflective surface of the collector, some of the radiation from the first irradiation means being scattered from the capillary tube in a scatter plane normal thereto;

first detection means for detecting radiation emitted from the sample including the reflected fluorescence;

second irradiation means for directly irradiating the sample as it migrates past the focal point, whereby the sample absorbs some of the radiation from said second irradiation means, some of the radiation from the second irradiation means being scattered from the capillary tube in a scatter plane normal thereto;

second detection means for detecting the amount of radiation absorbed by the sample; and spatial blocking means for blocking scattered radiation from reaching said first and second detection means, the spatial blocking means comprising an opaque blocking strip at the mouth of the collector for blocking the scattered radiation from reaching the first detection means, the spatial blocking means blocking only a minimal portion of the fluorescence at the mouth of the collector.

20. An apparatus as in claim 19 wherein the concave reflective surface of the collector has a parabolic shape to reflect fluorescence emitted from the sample at the focal point into a collimated beam.

21. An apparatus as in claim 19 wherein detections by the first and second detection means are performed simultaneously.

22. An apparatus as in claim 19 wherein the first irradiation means comprises a laser and the second irradiation means comprises an ultraviolet source.

23. An apparatus as in claim 19 further comprising means for effecting detection of fluorescence and absorbance alternately by the first and second detection means.

24. An apparatus as in claim 19 wherein radiation from the first irradiation means is directed through a first hole in the collector toward the sample within the capillary tube at the focal point at a right angle to the axis of the collector, some radiation from the first irradiation means being transmitted through the capillary tube and directed through a second hole in the collector, and wherein radiation from the second irradiation means is directed through a third hole in the collector toward the sample at the focal point along the axis of the collector, the second irradiation means being positioned behind the collector with the third hole in the collector located between the second irradiation means and the focal point.

25. An apparatus as in claim 19 further comprising third irradiation means for directly irradiating the sample within the capillary tube as the sample migrates past the focal point to emit fluorescence, some of the fluorescence being reflected off the reflective surface of the collector and substantially all of the fluorescence emanating from the mouth of the collector and being detected by a third detection means, the radiation from the third irradiation means having a different wavelength than the radiation from the first irradiation means.

26. An apparatus as in claim 19 wherein the spatial blocking means further comprises a wavelength filter spaced apart from the collector for blocking the scattered radiation from reaching the second detection means.

27. A capillary electrophoresis apparatus comprising:

a capillary tube defining a capillary separation channel through which sample components migrate;

means for causing electrophoresis of the sample into its components;

an axially-symmetrical concave fluorescence collector having a concave reflective surface, and defining a focal point and mouth, the capillary tube being positioned such that the sample components migrate past the focal point and being oriented at approximately a right angle to the axis of the collector;

first irradiation means for directly irradiating the sample components within the capillary tube as they migrate past the focal point so as to cause the sample components to emit fluorescence, some of the fluorescence being reflected off the reflective surface of the collector and substantially all of the fluorescence emanating from the mouth of the collector, the first irradiation means being positioned with respect to the capillary tube and the collector such that radiation from the first irradiation means irradiates the sample at a right angle to the capillary tube without first reflecting from the reflective surface of the collector, some of the radiation from the first irradiation means being scattered from the capillary tube in a scatter plane normal thereto;

first detection means for detecting radiation emitted from the sample components including the reflected fluorescence;

second irradiation means for directly irradiating the sample components as they migrate past the focal point, whereby the sample components absorb some of the radiation from said second irradiation means, some of the radiation from the second irradiation means being scattered from the capillary tube in a scatter plane normal thereto;

second detection means for detecting the amount of radiation absorbed by the sample components; and spatial blocking means for blocking scattered radiation from reaching the first and second detection means, the spatial blocking means comprising an opaque blocking strip at the mouth of the collector for blocking the scattered radiation from reaching the first detection means, the spatial blocking means blocking only a minimal portion of the fluorescence at the mouth of the collector.

28. An apparatus as in claim 27 wherein the concave reflective surface of the collector has a parabolic shape to reflect fluorescence emitted from the sample components at the focal point into a collimated beam.

29. An apparatus as in claim 27 wherein detections by the first and second detection means are performed simultaneously.

30. An apparatus as in claim 27 wherein the first irradiation means comprises a laser and the second irradiation means comprises an ultraviolet source.

31. An apparatus as in claim 27 further comprising means for effecting detection of fluorescence and absorbance alternately by the first and second detection means.

32. An apparatus as in claim 27 wherein radiation from the first irradiation means is directed through a first hole in the collector toward the sample components within the capillary tube at the focal point at a right angle to the axis of the collector, some radiation from the first irradiation means being transmitted through the capillary tube and directed through a second hole in the collector, and wherein radiation from the second irradiation means is directed through a third hole in the collector toward the sample components at the focal point along the axis of the collector, the second irradiation means being positioned behind the collector with the third hole in the collector located between the second irradiation means and the focal point.

33. An apparatus as in claim 27 further comprising third irradiation means for directly irradiating the sample components within the capillary tube as they migrate past the focal point to emit fluorescence, some of the fluorescence being reflected off the reflective surface of the collector and substantially all of the fluorescence emanating from the mouth of the collector and being detected by a third detection means, the radiation from the third irradiation means having a different wavelength than the radiation from the first irradiation means.

34. An apparatus as in claim 27 wherein the spatial blocking means further comprises a wavelength filter spaced apart from the collector for blocking the scattered radiation from reaching the second detection means.

* * * * *